United States Patent [19]

Showe et al.

[11] Patent Number: 5,079,147
[45] Date of Patent: Jan. 7, 1992

[54] DIAGNOSTIC PROBES AND METHODS FOR USING SAME TO DETECT BREAST CANCER

[75] Inventors: Louise C. Showe, Media; Richard C. Harvey, Philadelphia, both of Pa.

[73] Assignee: The Wistar Institute of Anatomy and Biology, Philadelphia, Pa.

[21] Appl. No.: 322,600

[22] Filed: Mar. 13, 1989

[51] Int. Cl.$^5$ .................... C07H 15/12; C12N 15/00; C12Q 1/68
[52] U.S. Cl. .......................................... 435/6; 536/27; 935/77; 935/78
[58] Field of Search ................ 435/6; 536/27; 935/77, 935/78

[56] References Cited

U.S. PATENT DOCUMENTS 4,701,409 10/1987 Croce ....................................... 435/6
4,752,566 6/1988 Collins et al. ............................ 435/6

OTHER PUBLICATIONS

Boehm et al., EMBO J., vol. 7, No. 7, 1988, pp. 2011–2017.
Ali et al., Science, vol. 238, Oct. 9, 1987, pp. 185–188.
A. Koufos et al., Nature, 316: 330–334 (1985).
S. H. Orkin et al., Nature, 309: 172–174 (1984).
E. R. Fearon et al., Nature, 309: 176–178 (1984).
I. U. Ali et al., Science, 238:185–188 (1987).
H. Klinger, Cytogenet. Cell Genet., 32: 68–84 (1982).
E. J. Stanbridge, Bioassays, 3: 252 (1985).
Lewis et al., Genomics, 3: 25–31 (1988) [Lewis I].
L. C. Showe et al., Ann. Rev. Imm., 5: 253–277 (1987).
Erikson et al., Science, 229: 784–786 (1985).
J. Boehm et al., EMBO J., 7(7):2011–2017 (1988).
Lewis et al., Nature, 317: 544–546 (1985) [Lewis II].
Williams et al., Cell, 36: 101–109 (1984).
Harvey et al., Oncogene, 4: 101–109 (1989).

*Primary Examiner*—Robert A. Wax
*Assistant Examiner*—Mindy B. Fleisher
*Attorney, Agent, or Firm*—Howson and Howson

[57] ABSTRACT

Novel DNA sequences located 5' to the chromosome 11p13 breakpoint are employed as diagnostic probes for breast cancers, T cell leukemias and WAGR associated with chromosome 11 abnormalities. Probe compositions and methods for diganostic assays are provided.

5 Claims, 3 Drawing Sheets

Figure 1

```
  1  GAATTCGTCC AAACCTGAGG ATCACAAGTC TCCACATTCT GAGTAGGAGG
 51  ATGAGGGTCT GAGTTAGGAT TTGGGTCCTG CGGGGCTTGC TAAGGAATCC
101  CTGATGGCCT AGGATTCCAC GCAGAGCACA TCTGGTGTGA GAGAGCTCGC
151  TGCAAGGGTG AAGGCTCCGC CTATCAGATA GACAACCAGG CCACCAAGAG
201  GCCCAGCCCT CCAAACCCTG GATTTGCAAC ATCCTCAAAG AACAGCAACG
251  GGCCTTGAGC AGAATTGAGA AGGAAATACC CCACCTGCCC TCAGCCGTTA
301  AGTGGGCTTT GCTATTCACA GGCTCTGGTG TCTGCACAGG GGAGATGGCA
351  CAGGCACCAT GGTGCATGGG TGCCAGGGCC TCCCGAGAAG GAACAGGTGC
401  AAAGCAGGCA ATTAGCCCAG AAGGTATCCG TGGGGCAGGC AGCCTAGATC
451  TGATGGGGGA AGCCACCAAG GATTACATCA TCTGCTCGGT GAGTACGGCT
501  TCATTAAGTT CTCTGATGAA TGGACGATTG CAAGGGAACT TTTTTCAATC
551  TTCAAGGAGC CAGAAGAAGT GGTGAATTAA AATTGGTCTT TTAAAATAAA
601  AATACTCCAA AGGGGTACAA GTCTTCAAGC TTGGC
```

Figure 2

```
    CCCACCCCAATAACCAATGGAAAAAAAAGTCAGAGAAAGAGAAATGGGGTTATAGAACAA
  1 ----------+---------+---------+---------+---------+---------+  60
    GGGTGGGGTTATTGGTTACCTTTTTTTTCAGTCTCTTTCTCTTTACCCCAATATCTTGTT

P  T  P  I  T  N  G  K  K  S  Q  R  K  R  N  G  V  I  E  Q

GAGGAATGTAAACAAATGAAtCTACTTACAGAAAAACAAAAGGCTAAAGCCCACAGTAAG
 61 ----------+---------+---------+---------+---------+---------+ 120
    CTCCTTACATTTGTTTACTTaGATGAATGTCTTTTTGTTTTCCGATTTCGGGTGTCATTC

E  E  C  K  Q  M  N  L  L  T  E  K  Q  K  A  K  A  H  S  K

AATCATCTTTTCTTCAAATCAGGGCAGAGGATATACAACAAAATAGGGCTCCTGAGATCT
121 ----------+---------+---------+---------+---------+---------+ 180
    TTAGTAGAAAAGAAGTTTAGTCCCGTCTCCTATATGTTGTTTTATCCCGAGGACTCTAGA

N  H  L  F  F  K  S  G  Q  R  I  Y  N  K  I  G  L  L  R  S

CAGGACTATCTTAAGGCTCTGATGAAAGAAGATGGGAGGGAAACAAGGGGAGACTGGCAG
181 ----------+---------+---------+---------+---------+---------+ 240
    GTCCTGATAGAATTCCGAGACTACTTTCTTCTACCCTCCCTTTGTTCCCCTCTGACCGTC

Q  D  Y  L  K  A  L  M  K  E  D  G  R  E  T  R  G  D  W  Q

CCCTGCCACTCACGTGATTAACTTAGCCATGACTCCCTGAGGCAAATGTCCTCAGCCAAG
241 ----------+---------+---------+---------+---------+---------+ 300
    GGGACGGTGAGTGCACTAATTGAATCGGTACTGAGGGACTCCGTTTACAGGAGTCGGTTC

P  C  H  S  R  D  *  L  S  H  D  S  L  R  Q  M  S  S  A  K

GAAACTGCTATTGCTATCATGCTTTTGGTTCACAACCCACCTTGAACTAATACATTTGAC
301 ----------+---------+---------+---------+---------+---------+ 360
    CTTTGACGATAACGATAGTACGAAAACCAAGTGTTGGGTGGAACTTGATTATGTAAACTG

E  T  A  I  A  I  M  L  L  V  H  N  P  P  *  T  N  T  F  D

AATGAAAATGAATTACTTTAAAAAAAAAAAGAAGAAGAAGAAGGAAAGGAGAGAGGAGAG
361 ----------+---------+---------+---------+---------+---------+ 420
    TTACTTTTACTTAATGAAATTTTTTTTTTCTTCTTCTTCTTCCTTTCCTCTCTCCTCTC

N  E  N  E  L  L  *  K  K  K  E  E  E  E  G  K  E  R  G  E

GAAGGGAAGGAGGAAAGAAAACTGCAAGCCTAATGATGGCATTCTTGGATATCCAATTGC
421 ----------+---------+---------+---------+---------+---------+ 480
    CTTCCCTTCCTCCTTTCTTTTGACGTTCGGATTACTACCGTAAGAACCTATAGGTTAACG

E  G  K  E  E  R  K  L  Q  A  *  *  W  H  S  W  I  S  N  C

TACAAAACTAGTTCACCCTCCATTTCTATATCCGCTGGTCACAGATTGGTGTGGG
481 ----------+---------+---------+---------+---------+----- 535
    ATGTTTTCATCAAGTGGGAGGTAAAGATATAGGCGACCAGTGTCTAACCACACCC

Y  K  S  S  S  P  S  I  S  I  S  A  G  H  R  L  V  W  ?
```

DIAGNOSTIC PROBES AND METHODS FOR USING SAME TO DETECT BREAST CANCER

The invention described herein was made in the course of work under a grant or award from the Department of Health, Education and Welfare.

BACKGROUND OF THE INVENTION

A variety of chromosomal aberrations have been associated with the occurrence of B cell and T cell cancers in humans and animals. Among such chromosomal abnormalities are deletions or inversions of all or a portion of certain gene sequences. Additionally, translocations of certain genes or fragments of genes from part of one chromosome to another chromosome or to a different part of the same chromosome have also been observed in various forms of cancer. Specific chromosomal translocations observed in human and animal tumors are thus believed to play a role in tumorigenesis.

The breakpoint of a chromosome rearrangement is that region at which the covalent bonds between nucleotides comprising the DNA backbone of one chromosome break and reform at a new position with other nucleotides in the same chromosome after a chromosomal deletion or with nucleotides derived from a different chromosome in a chromosomal translocation. The resulting chromosome may be a shorter version of the original chromosome due to a deletion or a hybrid chromosome formed by the joining between the original chromosome or a portion thereof with a portion of a different chromosome.

In many translocations the breakpoints lie near the loci of certain transforming genes. These observations have suggested that tumor development is partly due to the activation of these genes which normally perform the function of regulating cellular growth. In some cases a chromosomal abnormality may disable a suppressor gene which normally functions to repress cell proliferation. The transforming genes near the breakpoint or the point of disablement of the suppressor gene may thus initiate the unrepressed cellular development characteristic of tumor formation.

More specifically chromosome 11 has been identified as the site of a number of chromosomal abnormalities which have been observed and are correlated with the occurrence of certain human cancers. I. U. Ali et al, *Science*, 238:185–188 (1987) report a loss of heterozygocity for multiple loci on chromosome 11 which are correlated with the occurrence of certain aggressive breast tumors. Specifically, hybridization signals of most of the cases studied by Ali et al which were heterozygous for markers on the short arm of chromosome 11, were consistent with deletion of sequences on the short arm. Thus, the frequency of deletions on 11p in breast carcinomas was concluded to support the existence of regulatory sequences important in the genesis of breast tumors. Although about one in ten women develops breast cancer, presently, such aggressive breast carcinoma is not specifically detectable in its early stages from other less aggressive forms of breast cancer. Sequences on the short arm of chromosome 11 are implicated in the suppression of tumorigenicity of breast cancer derived Hela cells breast cancer derived cells [H. Klinger, *Cytogenet. Cell Genet.*, 32:68 (1982); E. J. Stanbridge, *Bioassays*, 3:252 (1985).]

In addition to its correlation with breast cancer, deletions and/or translocations on the short arm of chromosome 11 have also been associated with the occurrence of Wilms tumor, hepatoblastoma, hepatocellular carcinoma, and transitional cell carcinoma of bladder. Abnormalities at the 11p13 region have also been shown to be associated with embryonal carcinoma [A. Kaufos et al, Nature, 316:330–334 (1985)].

Wilms' tumor, aniridia, genito-urinary abnormalities and mental retardation collectively are referred to as WAGR. [See, S. H. Orkin et al, Nature. 309:172–174 (1984); and E. R. Fearon et al, Nature, 309:176–178 (1984)].

Wilms' disease is believed to be a hereditary disease which occurs in one out of every 50,000 newborns. This disease has also been observed to occur sporadically, i.e. without a hereditary basis, in five out of every 50,000 newborns. A recent report, Lewis et al, Genomics, 3:25–31 (1988) has shown that the breakpoint between chromosomes 11 and 14 in a patient having T cell acute lymphocytic leukemia (T-ALL) is closely linked to the locus for the WAGR.

Mapping studies have indicated the relative placement of certain translocation breakpoints on chromosome 11. L. C. Showe and C. Croce, *Ann. Rev. Imm* 5:253–277 (1987) review a particular region p13 on chromosome 11 which has been suggested to harbor a new oncogene or anti-oncogene which potentially plays an important role in the development of T cell leukemias. This report localizes that sequence to approximately the 5' portion of a breakpoint between chromosomes 11 and 14.

T. Boehm et al EMBO J., 7(7):2011–2017 (1988) disclose the detection of an 800 base pair region derived from chromosome 11p13 which contains a cluster of breakpoint sequences presumably involved in the pathogenesis of T-ALL. This report discloses a 0.65 kilobase region covered by the probe and provide a nucleotide sequence thereof.

There is a need in the art for agents for both diagnostic and therapeutic use which are capable of detecting and differentiating between different forms of breast cancer and other cancers and diseases associated with genetic abnormalities. Such diagnostic agents and tests would enable the selection of different types of presently available therapies for the condition so identified, and may also provide novel avenues of therapy.

SUMMARY OF THE INVENTION

The present invention provides as one aspect novel DNA sequences isolated from the short arm of chromosome 11 located 5' to the breakpoint of the translocation 11p13. The 5' DNA sequence, most proximal to the breakpoint, free from association with other mammalian DNA sequences is illustrated in FIG. 1. The second DNA sequence, which is located 5' of that in FIG. 1, free from association with other mammalian DNA sequences is illustrated in FIG. 2, with an accompanying amino acid sequence encoded thereby.

As another aspect of the invention there are provided DNA probes employing the DNA sequences described above. These sequences can be employed in diagnostic tests to detect and identify chromosomal translocations, deletions or insertions characteristic of certain aggressive breast carcinomas. Additionally, these probes containing DNA sequences located 5' to the 11p13 breakpoint may be employed to detect or diagnose the occurrence of Wilms' or WAGR disease. These probes may detect specifically the presence of hybrid chromosomes produced by a translocation in the breakpoint area between chromosomes 11 and 14. The DNA probes provided by this invention are also useful in identifying gene sequences or non-coding sequences located on translocated chromosomes that are involved in the malignant transformation of T cells and other cells involved in carcinoma and the conditions described above. These probes may be labeled with conventionally employed detecting agents or tags.

Another aspect of the invention is a method for diagnosing T cell neoplasms, comprising hybridizing a labelled DNA probe of the invention to a sample of a patient's DNA. The probe will hybridize to the sample DNA. The binding patterns of the probe with normal control DNA and with the sample chromosomal DNA are compared. and the differences, if any, between the DNA sample patterns and the pattern for normal chromosome 11 DNA detected. Alterations in the sample DNA from the normal pattern indicate the presence of a chromosomal rearrangement or translocation in chromosome 11. Such alterations signal the occurrence of malignant T cells in the patient.

Still another aspect is a method for diagnosing aggressive breast tumors, comprising hybridizing a labelled DNA probe of the invention to a sample of a patient's DNA obtained from a suspected breast tumor. The probe will hybridize to the sample DNA. The binding patterns of the probe with normal control DNA and with the sample chromosomal DNA are compared and the differences, if any, between the DNA sample patterns and the pattern for normal chromosome 11 DNA detected. Alterations in the sample DNA from the normal pattern indicate the presence of a chromosomal rearrangement or translocation in chromosome 11. Such alterations signal the occurrence of a malignant cancer cell from the suspected breast tissue.

As yet a further aspect of the invention there are disclosed therapeutic peptides which are encoded by DNA sequences which comprise one or more of the novel DNA sequences of the invention. The peptides of the invention are encoded by the novel DNA sequences and are thus provided free from association with other mammalian proteinaceous substances. These peptides may be produced by conventional chemical synthesis or via recombinant genetic engineering methods.

Still a further aspect of the present invention are polyclonal or monoclonal antibodies directed against epitopes on proteins coded for by the genes located on chromosome 11 in proximity to the 11p13 translocation breakpoint. These antibodies may be employed as diagnostic or therapeutic agents in the detection or therapy of disorders associated with the aberrant chromosomal sequences on the short arm of chromosome 11.

Yet a further aspect of the invention is a method for developing the polyclonal and monoclonal antibodies capable of binding to epitope on the proteins coded for by the genes located on the chromosomal sequence of chromosome 11, 5' to the 11p13 breakpoint. This method involves using the peptide sequences of the invention as antigenic substances eliciting the formation of such antibodies. Development of these antibodies employ conventional methodologies known to those of skill in the art.

Finally the invention provides a method for producing the peptides of the present invention by culturing a suitable host cell transformed with a DNA sequence coding for a gene located on chromosome 11 in operative association with appropropriate expression control sequences.

The products and methods of this invention permit the detection and identification of T cell neoplasms, breast carcinoma, and WAGR in patients in the early stage of these diseases. The invention thus does not require manifestation of overt symptoms for an accurate diagnosis.

Other aspects of the present invention will be further explored in the following detailed description of the preferred embodiment thereof.

BRIEF DESCRIPTION OF THE DRAWINGS

FIG. 1 illustrates a human DNA sequence located 5' to the 11p13 breakpoint;

FIG. 2 depicts human DNA sequences from chromosome 11 located 5' of the sequence in FIG. 1, and also illustrates a sequence of amino acids in one reading frame of this sequence;

FIG. 3 illustrates restriction maps of the T cell receptor delta chain (Tcr-d) of several human chromosomes and translocation with chromosome 11 involving this region.

DETAILED DESCRIPTION OF THE INVENTION

Figure 3A:
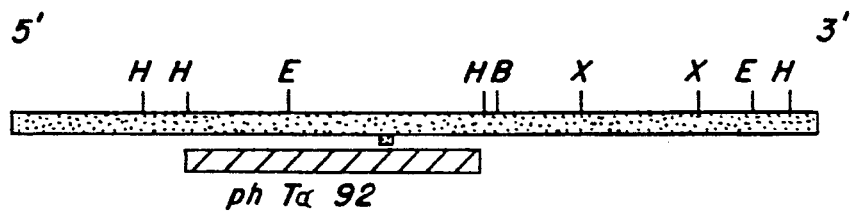
FIG. 3a depicts a translocation in Tcr-d between chromosomes 11 and 14 from DNA of a T-ALL patient.

The present invention provides a number of DNA sequences useful as diagnostic probes for the diagnosis of breast cancer characterized by abnormalities on the short arm of chromosome 11. Additional DNA sequences of the invention may also be employed in diagnosing chromosomal abnormalities associated with T cell acute lymphocytic leukemia, embryonal cancer, and WAGR characterized by aberrant sequences on the short arm of chromosome 11, 5' to the 11p13 breakpoint.

The novel DNA sequences according to the invention include sequences the same or substantially identical to the sequences illustrated in FIGS. 1 and 2, or fragments thereof. Similarly, DNA sequences which differ in nucleotide or codon sequence due to the degeneracies of the genetic code or allelic variations (naturally-occurring base changes in the species population which may or may not result in an amino acid change) are also encompassed by this invention. Variations in the DNA sequences of the invention which are caused by point mutations or by induced modifications are also encompassed in the invention. Such derivatives of the disclosed sequences are included in this invention.

The novel DNA sequences of the present invention or fragments thereof may be chemically synthesized in a conventional manner or produced via recombinant techniques. For example, these sequences may be cloned into plasmid vectors for preparing large quantities of probes using standard vectors and host cells, such as described in T. Maniatis et al, *Molecular Cloning (A Laboratory Manual)*, Cold Spring Harbor Laboratory (1982).

Additional sequences from this region of chromosome 11 may be derived from available genomic DNA libraries and chromosome 11 cloned DNA. Genomic libraries have been prepared from the DNA from any of these sources by standard techniques, e.g. such as described in J. J. Toole et al, Nature, 312:342-346 (1984), or in phages as described in U.S. Pat. No. 4,701,409.

As described below in the examples showing how the sequences of FIGS. 1 and 2 were obtained, desired additional fragments of DNA of the present invention may be obtained by screening independent recombinant phages with one or more probes of the present invention (FIGS. 1 or 2 or fragments thereof) to expand the cloned region on chromosome 11. This procedure may be used to isolate and identify a gene sequence located near the 11p13 breakpoint of the hybrid 11/14 chromosome present in the T cell line.

DNA sequences of the invention may be used as probes to locate aberrant sequences, e.g., rearrangements, translocations or deletions, characteristic of breast cancer, WAGR or T cell leukemias which are located 5' to the 11p13 breakpoint on chromosome 11 in the following manner.

After the occurrence of such a translocation or deletion in chromosome 11, the DNA sequence forming the rearranged chromosome 11 or a hybrid chromosome 11/14 has a restriction map that differs from the original germ line DNA. Thus, the occurrence of a deletion, translocation or other abnormality in chromosome 11 can be identified by conventional restriction map analysis using the DNA sequences of this invention as probes.

For example, in a diagnostic method for detecting T-cell neoplasms in a human, T-cells from a human patient are isolated and DNA extracted therefrom to form a test sample. The DNA is then restricted by treatment with restriction enzymes, size-fractionated on an agarose gel and transferred to a nylon filter. The test sample is then contacted with a DNA probe of the present invention (optionally labelled with a detectable tag) containing a sequence of at least 200 nucleotides in length. For example, the entire FIG. 1 sequence may be used as a probe, or only smaller portions thereof. The contact between the probe DNA and the test sample DNA or control DNA is performed under conditions where homologous DNA-DNA hybrids form and are stable.

The restriction map representing the pattern of DNA fragments of specific sizes which result when the control normal chromosome 11/probe hybrid is cut with one or more conventionally used restriction enzymes is different from the fragments of DNA which result when a sample DNA having a deletion or translocation therein/probe hybrid is cut with the same enzymes. A difference in restriction pattern in the test sample obtained with the probe of the present invention thus indicates a chromosomal defect related to the disease in question.

In a similar manner DNA sequences of the present invention may be used in a diagnostic method for detecting aggressive breast cancers in a human. This method also includes isolating cells from a suspected mass or tumor in a human breast. The DNA is extracted from these breast tumor cells, restricted, size fractionated and transfered to filters to form a test sample. The test sample is then contacted with an optionally labelled DNA probe of the invention containing at least 200 nucleotides in length under conditions where homologous DNA-DNA hybrids form and are stable. The restriction patterns of the test sample are compared with a normal control to determine whether the sample demonstrated chromosomal aberrations indicative of breast cancers.

In some instances of illness caused by chromosomal sequence deletion, the probe sequence may be lost and consequently, the signal intensity provided by the tag on the probe reduced. The amount of DNA-DNA hybrids formed between the probes and the test sample in these assays are then quantitated; and compared to the amount of DNA-DNA hybrids formed as determined by signal to the amount formed with a control sample of DNA. Where the patient providing the sample DNA has a condition, such as Wilms disease, related to a chromosomal deletion, the signal for the patient sample may be decreased or rearranged in comparision to the signal provided by the normal control. Such signal disparities, if not positive diagnostic indications of disease, are nevertheless indications that further diagnostic methods should be employed to confirm the chromosomal deletion diagnosis.

DNA probes for use in these diagnostic methods may be selected from any of the DNA sequences or fragments thereof identified above or allelic variants thereof. The sequence of FIG. 1 or fragments thereof is particularly useful in such assays as probes for the detection of T-ALL breakpoints and chromosomal translocations indicative of breast cancers. The sequence of FIG. 2 or fragments thereof is particularly useful in detecting chromosomal deletions characteristic of Wilms disease or aniridia. Other suitable probes may be synthesized or derived from these or other chromosome 11 sequences. These probes may be produced by chemical synthesis of the sequences provided in FIGS. 1 and 2, or replicated in conventional E. coli vectors and cells as described in Maniatis et al, supra.

In order to perform the hybridizations required in the diagnostic assays described above, it is desirable that the probe be single stranded. Thus, if the probe is double stranded, it should be denatured to single stranded or partially single-stranded form. Means for denaturing are well known in the art, including alkali or heat treatment.

In a similar manner the coding DNA sequences of the present invention, e.g., the sequence of FIG. 2, may be used in RNA assays to diagnose T cell leukemias, breast cancers, and/or WAGR disease. This method would include again the steps of isolating the cells in question from a human and extracting RNA sequences therefrom to form the test sample. The test sample is then contacted with a single stranded DNA probe from a DNA coding sequence under conditions where homologous RNA-DNA hybrids form and are stable. In such a method the test samples are examined for both qualitative and quantitative differences from the normal sequences.

In DNA diagnostic assays, such as Southern Blot, a change in DNA sequence pattern from the test sample to the DNA probe or a loss of signal which would indicate a deletion in the chromosomal sequence of the cells in question is determined. Alternatively, RNA diagnostic assays examine an increase or decrease or alteration in size of the message encoding a gene product, wherein the gene is located on the short arm of chromosome 11. Such conditions are well known in the art. [See, e.g., Maniatis et al, supra].

Means for detecting the DNA-DNA or RNA-DNA hybrids are many and well known, but often involve use of radiolabeled probes and nucleases which degrade single stranded DNA or RNA. Appropriate detectable tags and labels are discussed in further detail below.

In the diagnostic methods of the invention, a parallel sample to the test sample is employed to provide the control. The control sample consists of an equivalent amount of DNA, RNA or protein extracted from cells, preferably in the same manner as those of the test sample. The amount of DNA sequence, RNA message or protein can readily be determined employing techniques well known in the art, such as spectrophotometric techniques. The cells used for preparing the control sample may be selected from the group consisting of cells from a normal human where possible, cells from established appropriate normal cell lines, and normal cells from the human who is being screened for the neoplasm.

For example, where the diagnostic assay is for T cell leukemia, the cells or the control sample may be selected from T cells of a normal human, T cells from an established normal human cell line, and normal non-T cells from the patient contributing the T cell test sample. The control cells for the diagnostic assay used to detect the presence of breast cancers would be selected in the same way. The test samples and control samples in any of these assays should be prepared in parallel under similar conditions.

As another facet of this invention, the above-disclosed DNA coding sequences selected from chromosomal sequences 5' to the 11p13 breakpoint, e.g., FIG. 1 or FIG. 2, may be expressed to provide proteins, polypeptides or other proteinaceous products for use as potential therapeutic agents. For example, the DNA sequence responsible for encoding a putative suppressor gene on chromosome 11 may be employed to express the protein by conventional chemical synthesis of the amino acid sequence encoded thereby or by recombinant genetic engineering techniques. This protein may be employed as a therapeutic agent to provide suppression of the relevant oncogene in patients with breast or other cancer associated with the aberration of chromosome 11. FIG. 2 illustrates a putative protein sequence.

The suppressor protein or other protein or polypeptide encoded by these novel DNA sequences may be produced by culturing a suitable cell or cell line, which has been transformed with a DNA sequence coding for the putative suppressor polypeptide under the control of known regulatory sequences. Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, *Nature,* 293:620-625 (1981), or alternatively, Kaufman et al, *Mol. Cell. Biol.,* 5(7):1750-1759 (1985) or Howley et al, U.S. Pat. No. 4,419,446. Another suitable mammalian cell line is the monkey COS-1 cell line. A similarly useful mammalian cell line is the CV-1 cell line.

Similarly useful as host cells suitable for the present invention are bacterial, yeast or insect cells. For example, the various strains of *E. coli* (e.g., HB101, MC1061) various strains of *B. subtilis,* Pseudomonas, other bacilli and the like may be employed as host cells. Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering,* 8:277-298 (Plenum Press 1986) and references cited therein.

The present invention also provides vectors for use in the method of expression of polypeptides encoded by one or more of the DNA coding sequences of the invention. These vectors contain the novel DNA sequences which code for polypeptides of the invention. The vector employed in the method also contains selected regulatory sequences in operative association with the DNA coding sequences of the invention and capable of directing the replication and expression thereof in selected host cells.

The DNA coding sequences and protein products which they encode may also be employed to generate polyclonal or monoclonal antibodies which are immunoreactive with the suppressor proteins or other proteins encoded by sequences located on chromosome 11. Antibodies can be produced by immunization of animals, such as mice, rabbits and the like, with the proteins or immunogenic fragments thereof or with a fusion protein consisting of a portion of the beta-galactosidase protein of *E. coli* and a portion of the suppressor or other proteins encoded by DNA sequences of the invention. Alternatively, monoclonal antibodies can be generated using immortalized cell lines to provide uniform and continual antibody sources. Techniques for generating such antibodies are well known in the art. Appropriate antibodies can be screened using the natural gene products of the DNA sequences or the fusion protein discussed above.

Antibodies thus formed may also be employed as diagnostic agents in assays to determine the presence of protein sequences likely to be associated with breast cancer or the other conditions described above. In such an assay, proteins from cells associated with the neoplasm may be extracted by any of the many means known in the art as described above. For example, cells may be lysed by a detergent or by mechanical means. If desired, nucleic acids can be removed from the cell preparation by enzymatic digestion or by precipitation with agents such as streptomycin. Once again, such means are well known in the art. The extracted proteins from the affected cells may be contacted with the antibody under suitable conditions for antibody-antigen complex formation. Generally, such conditions are physiological conditions. The protein extract may be fractionated by SDS-PAGE and then bound to a solid support.

Means of detection of the probe DNA-DNA or probe DNA-RNA hybridization complexes described above or the antibody-antigen complexes will depend upon the method of tagging used. For example, radiolabel tags can be detected by autoradiography or scintillation counting, while the products of enzyme-linked probes or antibodies can be detected colorimetrically and spectrophotometrically. Directly detectable tags which may be used include radionuclides (e.g., phosphorus-32, sulfur-35, carbon-14 or iodine-125 labeled nucleotides), fluorescent compounds (e.g., fluorescein or rhodamine derivatives) or moieties directly detectable by other means (e.g., nitrophenol detectable colorimetrically). Indirectly detectable tags include agents that can serve as antigenic determinants, affinity ligands, antigens or antibodies recognizable through immunochemical or other affinity reactions, e.g., biotinated nucleotides. Other indirect tags include apoenzymes, co-enzymes, enzymatic modifiers, enzymatic cofactors or enzymes attached to a probe whose presence can be determined by addition of the substrate for the enzyme and quantification of the enzymatic substrate or reaction product.

In addition to diagnostic uses of the DNA probes and antibodies of the present invention, such probes and antibodies may also be used as research tools.

The following examples illustrate embodiments of the invention and are not intended to limit the scope of the invention.

EXAMPLE 1

Obtaining the Sequence of FIG. 1

A DNA preparation

DNA was extracted from patient samples (normal and T-ALL) and cell lines essentially as described by M. Poncz et al, *Hemoglobin,* 6:27-36 (1982). Cells were pelleted, washed with phosphate buffered saline and digested overnight at 37° C. in 10 mM Tris-HCl (pH 8.0), 10 mM EDTA, 10 mM NaCl, 0.5% sodium dodecyl sulfate (SDS) and 100 µg ml$^{-1}$ proteinase K. The solution was extracted twice with phenol, once with phenol/chloroform (1:1) and once with chloroform. It was then carefully poured through 2.5 volumes of 95% ethanol at room temperature and the DNA was spooled out and dissolved in 1×TE.

B. Genomic Library Preparation

Genomic libraries of T-ALL patient and human placental DNA (Sigma Chemical, St. Louis, Miss.) were constructed in lambda phage EMBL3a essentially as described by A. M. Frischauf et al, *J. Mol. Biol.,* 170:827-842 (1983). Partial Sau 3a digests were cloned into the BamHI site of EMBL3a. The libraries were screened as described in T. Maniatis et al, cited above. The clones were routinely mapped using single and double digests of BamHI, EcoRI, HindIII, SalI, and XbaI. Non repetitive probes were subcloned for individual genomic clones and used to rescreen patient or normal genomic DNA libraries. Probe pHTalpha92 is a sequence from normal chromosome 14, as shown in FIG. 3a. When used to screen a patient's library, this probe isolated a genomic clone containing a chromosome 11/chromosome 14 translocation.

Figure 3B:
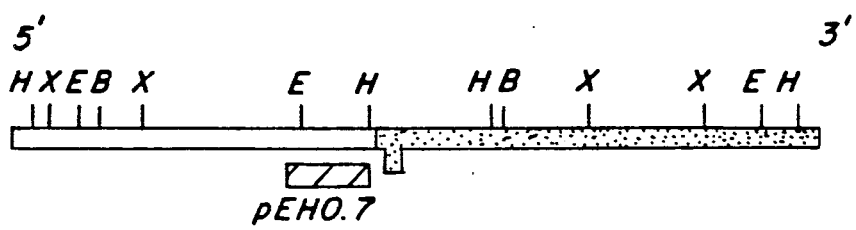
FIG. 3b depicts a restriction map of Tcr-d of chromosome 14 from the DNA of a normal patient.
Figure 3C:
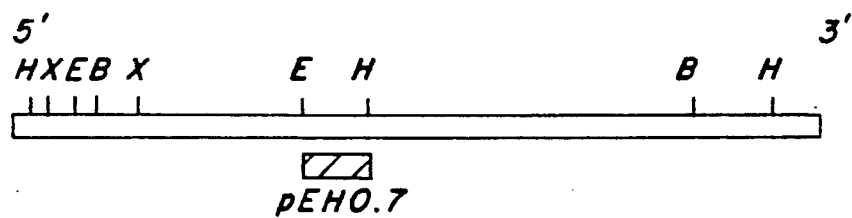
FIG. 3c depicts a restriction map of chromosome 11 from the DNA of a normal patient. The open bar designates sequences arising from chromosome 14; the solid bar indicates sequences arising from chromosome 11. The hatched boxes show the location of genomic probes, pEH0.7 and phTalpha92, used to identify the presence of chromosome 11 sequences in the translocation. Restriction enzyme abbreviations are the following: H is HindIII; X is XbaI; E is EcoRI; B is BamHI.

A piece of DNA from the region where the restriction maps of the two chromosome sequences diverged was subcloned. A subcloned probe called pEH0.7 (see FIG. 3b and 3c) was shown to derive from chromosome 11. This sequence hybridized to a human/mouse somatic cell hybrid containing only chromosome 11.

pEH0.7 DNA to be sequenced was subcloned into either M13 or pUC18/19 vectors [C Yanisch-Perron et al, *Gene.* 33:103-109 (1985)]. Single stranded sequencing was done by dideoxy chain termination [F. Sanger et al, (1977)] or by Sequenase (US Biochemical, Cleveland, Ohio) protocols. The single stranded nucleotide sequence for pEH0.7 is reported in FIG. 1.

Following procedures substantially as described above, the DNA sequence of FIG. 2 was obtained using a genomic clone pHTalpha79 which is located 3' of the breakpoint on chromosome 14. Probe pHTalpha79 binds both chromosome 11 and 14. The FIG. 2 sequence was thus obtained from chromosome 11 at a point 5' to the chromosome 11 breakpoint. Double stranded sequencing was done according to the method of R. Kraft, et al, Bio Techniques, 6:544-547 (1988).

EXAMPLE 2

Use of Probes in Diagnostic Assays

The probes of the present invention were employed in the following procedures including Southern Blot assays and Northern Blot assays of DNA samples from patients with T-ALL.

A. Probe Amplification and Labelling

A selected probe (e.g., all or a portion of the sequence of FIG. 1 or FIG. 2) was subcloned into pUC18 or pUC19 [C. Yanisch-Perron et al, cited above] and amplified in *E. coli.* The purified probe was labelled with [$^{32}$P] using either random hexamer/primer extension [A. P. Feinberg et al, *Anal. Biochem.,* 132:6-13 (1983)] or nick translocation (BRL Nick Translation Kit, Bethesda, Md.). The labelled probe is now ready for use in a diagnostic assay.

B. Northern Blot Assays

T-ALL tumor cells were obtained as primary patient samples [D. L. Williams et al, *Cell,* 36:101-109 (1984)]. Total nuclear and/or cytoplasmic RNA was extracted (when possible) from patients with T/ALL and normal patients using standard procedures. RNA is fractionated on gels under denaturing conditions and then blotted to nitro-cellulose and hybridized with a radioactive probe, consisting of the sequence of FIG. 1, and a radioactive probe consisting of the sequence of FIG. 2. Transcript levels are quantitated by densitometric scanning of autoradiographic intensities and normalized to an internal control by rehybridizations of the filters with a probe for a housekeeping gene such as PGK, HGPRT, or enolase.

C. Southern Blot Assays

The probes of the present invention may also be used in Southern blot assays. Hybridization of Southern blots is performed essentially as described by G. M. Church et al, *Proc Natl. Acad. Sci., USA,* 81:1991-1995 (1984), with the following modifications. The hybridization solution is 0.5M NaHPO$_4$ (pH 7.2), 1 mM EDTA, 1% bovine serum albumin and 2% SDS. Hybridization was done for 4-16 hours at 68° C. with a final probe concentration of 100-200 ng ml$^{-1}$. Blots were washed according to the GeneScreen Plus protocol (NEN, Boston, Mass.) to a final wash of 0.1×SSC, 1% SDS. Blots were typically exposed for 8 hours-2 days at —70° C. using Kodak XAR-5 film (Rochester, N.Y.) and two Lightning Plus intensifying screens (DuPont, Wilmington, Del.).

2.5 to 10 µg each DNA was digested to completion with the indicated restriction enzymes. Samples were electrophoresed in 1×TBE through 0.8% agarose gels (BRL Ultrapure agarose, Bethesda, Md.) containing ethidium bromide as described by T. Maniatis et al, supra. The gels were photographed and soaked in 0.25N HCl for 20 minutes. DNA was then transferred to GeneScreen Plus (NEN, Boston, Mass.) for 4 hours in 0.4N NaOH. The membrane was neutralized in 250 mM Tris-HCl/6×SSC for 5 minutes and then dried completely.

Comparing the DNA sample restriction patterns from the patients with control DNA patterns indicates the presence of chromosomal alterations in the sample DNA patterns indicative of T-ALL.

Using the probes of FIGS. 1 or 2 or fragments thereof, Northern and Southern Blots may be conducted in the same manner using DNA samples from patients with breast tumors. Pattern comparision indicates the presence of abnormalities on the short arm of chromosome 11.

Similar assays may employ the probes of the invention for the diagnoses of Wilms' disease, aniridia and other defects on chromosome 11 or 14.

EXAMPLE 3

Preparing Peptide Fragments from FIG. 2 Sequence

Synthetic peptides are prepared [A. Giallongo et al, *Science*, 222:430-433 (1983)] from the sequences of the carboxyl and amino terminal ends of the sequence of FIG. 2 and any additional sequences deemed suitable in the predicted amino acid sequence. Peptides are synthesized using a Vega 250 peptide synthesizer. The crude product is purified by gel filgration and reverse phase chromatography. The material is coupled to keyhole limpet hemocyanin through a tyrosine residue, added if necessary, for coupling purposes.

The pUR plasmid expression vector, [U. Ruther et al, *EMBO J.*, 2:1791-94 (1983)] or other appropriate vectors are used to express these synthetic peptide sequences. The host used is *E. coli* JM109 [Viera et al, *Gene*, 19:259-68 (1982)] or other appropriate host cells. The isolated and sequenced cDNA are inserted in frame with the translation initiation codon provided on the expression vector. The rate of synthesis of proteins in *E. coli* transformed with the vector containing the insert before and after induction are studied by pulse labeling. The expressed protein is purified from *E. coli* using essentially the procedure described for the purification of the influenza virus NS1 protein [Young et al, *Proc. Natl. Acad. Sci.*, 80:6105-6109 (1983)].

EXAMPLE 4

Preparation of Antisera from FIG. 2 protein

New Zealand white rabbits are inoculated subscapularly with 5 doses of 100 μg each of purified protein or synthetic peptides in Freund's adjuvant over a two-month period. The appearance of antibodies is monitored by radioimmunoassay and immunoblot analysis as follows.

First, sodium dodecylsulfate polyacrylamide gel electrophoresis (SDS-PAGE) is performed on the antibody protein. After SDS-PAGE, proteins are electrophoretically transferred to nitrocellulose. The protein blot is incubated in RIPA buffer (0.05M Tris pH 7.4, 0.15M NaCl, 1% Triton X100, 1% DOC 0.1% SDS) containing 0.5% BSA for 30 minutes, then incubated in 10 ml of RIPA buffer containing 15 μl rabbit antiserum for 1 hour. The specifically bound antibody is detected by incubation with $^{125}$I-labeled protein A followed by autoradiography or enzyme-linked immunoassay (ELISA).

To store the antisera for further use of the antibody, blood from the rabbits is collected from the marginal ear vein, followed by coagulation at 4° C. overnight and centrifugation at 5,000×g. Serum is stored at −70° C. Monoclonal antibody may be generated according to standard methods.

Numerous modifications and variations in practice of this invention are expected to occur to those skilled in the art. For example, diagnostic assays other than those illustrated in the above Examples may employ the DNA sequences of this invention. Additionally, the proteins encoded by FIG. 2 may be employed in other diagnostic assays. Such modifications are believed to be encompassed by the appended claims of this invention.

We claim:

1. A DNA having a sequence useful as a diagnostic probe consisting of the sequence of FIG. 1.

2. A DNA having a sequence useful as a diagnostic probe consisting of the sequence of FIG. 2.

3. A diagnostic probe useful for detecting chromosomal aberrations associated with breast cancer and T cell leukemia consisting of a DNA having a sequence selected from the group consisting of FIG. 1 and FIG. 2 optionally labelled with a detectable tag.

4. A method for diagnosing breast cancer associated with translocated chromosomal sequences on chromosome 11 comprising the steps of:

hybridizing a labelled DNA probe comprising a DNA sequence optionally labelled with a detectable tag and selected from the group consisting of FIG. 1 and FIG. 2, said probe hybridizing to a region of DNA lying between a restriction site of a hybrid chromosome of malignant T cell and the 11p13 breakpoint of said chromosome, said restriction site being unique to said region;

identifying the pattern of restricted chromosomal DNA segments to which the DNA probe hybridizes; and detecting differences between the pattern identified for said patient DNA sample and the pattern detected for restricted normal chromosome 11 DNA, whereby a difference in pattern between said patient sample and said control pattern indicates the presence of chromosomal aberration.

5. A method for diagnosing T cell leukemias associated with translocated chromosomal sequences on chromosome 11 comprising the steps of:

hybridizing a labelled DNA probe comprising a DNA sequence optionally labelled with a detectable tag and selected from the group consisting of FIG. 1 and FIG. 2, said probe hybridizing to a region of DNA lying between a restriction site of a hybrid chromosome of malignant T cell and the 11p13 breakpoint of said chromosome, said restriction site being unique to said region;

identifying the pattern of restricted chromosomal DNA segments to which the DNA probe hybridizes; and detecting differences between the pattern identified for said malignant T cell and the pattern detected for restricted normal chromosome 11 DNA.

* * * * *

UNITED STATES PATENT AND TRADEMARK OFFICE
CERTIFICATE OF CORRECTION

PATENT NO. : 5,079,147
DATED : January 7, 1992
INVENTOR(S) : Louise C. Showe and Richard C. Harvey It is certified that error appears in the above-identified patent and that said Letters Patent is hereby corrected as shown below:

Col. 1, line 7, after "Welfare", insert -- , specifically Grant No. CA 25875. The Government has certain rights in this invention. --

Signed and Sealed this

Thirtieth Day of March, 1993

Attest:

STEPHEN G. KUNIN

*Attesting Officer*   Acting Commissioner of Patents and Trademarks